United States Patent [19]
Sekiguchi et al.

[11] Patent Number: 5,977,402
[45] Date of Patent: Nov. 2, 1999

[54] PROCESSES FOR PREPARING 4-TERT.-BUTYLCYCLOHEXANOL AND 4-TERT.-BUTYLCYCLOHEXYL ACETATE

[75] Inventors: Masahito Sekiguchi; Shin Tanaka, both of Ehime, Japan

[73] Assignee: Sumitomo Chemical Company, Limited, Osaka, Japan

[21] Appl. No.: 09/064,035

[22] Filed: Apr. 22, 1998

Related U.S. Application Data

[63] Continuation-in-part of application No. 08/684,063, Jul. 19, 1996, abandoned.

[30] Foreign Application Priority Data

Jul. 20, 1995 [JP] Japan ..................................... 7-184238

[51] Int. Cl.$^6$ .............................. C07C 67/00; C07C 35/08
[52] U.S. Cl. .......................... 560/239; 568/835; 568/834; 568/822
[58] Field of Search ............................ 560/239; 568/835, 568/834, 822

[56] References Cited

U.S. PATENT DOCUMENTS

| | | |
|---|---|---|
| 2,927,127 | 3/1960 | Somerville et al. . |
| 4,343,955 | 8/1982 | Oshima et al. . |
| 4,551,564 | 11/1985 | Otte et al. . |
| 5,107,038 | 4/1992 | Weinstein . |
| 5,160,498 | 11/1992 | Weinstein . |

FOREIGN PATENT DOCUMENTS

| | | |
|---|---|---|
| 0427965 | 4/1991 | France . |
| 42-13938 | 8/1967 | Japan . |
| 52-41255 | 10/1977 | Japan . |
| 54-122253 | 9/1979 | Japan . |
| 60-34526 | 8/1985 | Japan . |
| 3-173842 | 7/1991 | Japan . |
| 3-206061 | 9/1991 | Japan . |
| 4-60456 | 9/1992 | Japan . |

OTHER PUBLICATIONS

"Stereoselective Hydrogenation of Aromatic Compounds Using Highly Active Mono–and Bimetallic . . . " by R. Burmeister et al., Science and Tech. in Catalysis 1994, pp. 343–346.

"Stereoselective Hydrogenation of Unhindered Cyclohexanones to Axial Alcohols with Rhodium Catalyst" by S. Nishimura et al., Chemistry Letters, pp. 963–966, 1977.

"Stereoselective Hydrogenation . . . ", by S. R. Konuspaev et al., Kinet Katal., 34(1), pp. 89–94, 1993.

S.R. Konuspaev et al., Stereoselective Hydrogenation of . . . , Kinet Katal, vol. 35, No. 1, pp. 72–75, 1994.

Izv. Akad. Nauk. Kaz. SSR, Ser. Khim,(2)pp. 49–52, 1990 (w/English abstract) S. R. Konuspaev et al.

Izv. Akad. Nauk. Kaz. SSR, Ser. Khim, 1, pp. 13–17, 1990 (with English abstract) S. R. Konuspaev et al.

Maslo–Zhir. Prom–st., 1, p. 27, 1987 (with English abstract) Konuspaev et al.

Maruzen Sekiyu Giho, No. 16, pp. 77–87, 1971, Yokogawa et al.

*Primary Examiner*—Samuel Barts
*Assistant Examiner*—Rosalynd Keys
*Attorney, Agent, or Firm*—Birch, Stewart, Kolasch & Stewart

[57] ABSTRACT

4-tert.-Butylcyclohexanol having a larger content of its cis-isomer is prepared by hydrogenating 4-tert.-butylphenol in a solvent in the presence of a rhodium catalyst and a compound selected from the group consisting of hydrogen chloride and (anhydrous) sulfuric acid. Furthermore, 4-tert.-butylcyclohexanol obtained by the above hydrogenation is acetylated to give 4-tert.-butylcyclohexyl acetate.

9 Claims, No Drawings

PROCESSES FOR PREPARING 4-TERT.-BUTYLCYCLOHEXANOL AND 4-TERT.-BUTYLCYCLOHEXYL ACETATE

This application is a continuation-in-part of U.S. application Ser. No. 08/684,063, filed Jul. 19, 1996, now abandoned.

BACKGROUND OF THE INVENTION

1. Field of the Invention

The present invention relates to a process for preparing 4-tert.-butylcyclohexanol containing the larger amount of the cis-isomer by hydrogenating 4-tert.-butylphenol under specific conditions. The present invention also relates to a process for preparing 4-tert.-butylcyclohexyl acetate by acetylating 4-tert.-butylcyclohexanol which is obtained by the process described above.

2. Description of the Prior Art 4-tert.-Butylcyclohexyl acetate is widely used as a perfume for cosmetics including soaps, and fragrance of its cis-isomer is more favorable than that of its trans-isomer. To prepare 4-tert.-butylcyclohexyl acetate having a high cis-isomer content, it is desired to provide a process for preparing 4-tert.-butylcyclohexyl containing the larger amount of the cis-isomer because 4-tert.-butylcyclohexanol is used as a raw material of 4-tert.-butylcyclohexyl acetate.

In general, 4-tert.-butylcyclohexanol is prepared by hydrogenating 4-tert.-butylphenol.

JP-B-42-13938 discloses a process for preparing 4-tert.-butylcyclohexanol comprising catalytically reducing 4-tert.-butylphenol in the presence of a rhodium base catalyst.

MARUZEN OIL TECHNICAL REVIEW (MARUZEN SEKIYU GIHO) (1971) page 77 discloses a process for preparing 4-tert.-butylcyclohexanol comprising hydrogenating 4-tert.-butylphenol in the presence of various transition metals of the 8 to 10 Groups of the Periodic Table.

JP-A-54-122253 discloses a process for preparing a cis alkylcyclohexanol comprising hydrogenating an alkylphenol in the presence of a ruthenium-alumina catalyst.

U.S. Pat. No. 2,927,127 discloses a process for preparing 4-tert.-butylcyclohexanol comprising hydrogenating 4-tert.-butylphenol in ethanol in the presence of the rhodium catalyst.

JP-A-3-173842 discloses a process for preparing 4-tert.-butylcyclohexanol comprising hydrogenating 4-tert.-butylphenol in the presence of a combined catalyst of Rh supported on a carrier and a boron fluoride type acid such as $HBF_4$.

However, the cis-isomer content in 4-tert.-butylcyclohexanol which is prepared by the processes disclosed in JP-B-4213938, MARUZEN OIL TECHNICAL REVIEW and JP-A-54-122253, is still insufficient. The process of U.S. Pat. No. 2,927,127 achieves a high cis-isomer content, but the reaction must be performed under a high hydrogen pressure. Further, in the process of JP-A-3-173842, since the process uses the boron fluoride type acid, a workload is required to recover fluorine and boron, and generated acids such as HF corrode a production equipment.

SUMMARY OF THE INVENTION

An object of the present invention is to provide a process for preparing 4-tert.-butylcyclohexanol having a high cis-isomer content, which can be carried out under a mild condition and which does not require the use of a boron fluoride type acid.

Another object of the present invention is to provide a process for preparing 4-tert.-butylcyclohexyl acetate having a high cis-isomer content.

As the result of an extensive study made by the present inventors with the aim of achieving the above objects, it has been found that 4-tert.-butylcyclohexanol containing the larger amount of the cis-isomer can be obtained by hydrogenating 4-tert.-butylphenol under certain mild conditions, and 4-tert.-butylcyclohexyl acetate having the high content of the cis-isomer thereof can be obtained by acetylating 4-tert.-butylcyclohexanol which has been prepared by the above process.

Thus, the present invention provides a process for preparing 4-tert.-butylcyclohexanol comprising hydrogenating 4-tert.-butylphenol in a solvent in the present of (1) at least one rhodium catalyst selected from the group consisting of metal rhodium and rhodium compounds supported on a carrier and (2) a compound selected from the group consisting of hydrogen chloride and (anhydrous) sulfuric acid, wherein hydrogen chloride or (anhydrous) sulfuric acid is present in an amount of 1.4 to 10 moles per one mole of elemental rhodium.

The present invention further provides a process for preparing 4-tert.-butylcyclohexyl acetate comprising the steps of:

hydrogenating 4-tert.-butylphenol in a solvent in the presence of (1) at least one rhodium catalyst selected from the group consisting of metal rhodium and rhodium compounds supported on a carrier and (2) a compound selected from the group consisting of hydrogen chloride and (anhydrous) sulfuric acid, wherein hydrogen chloride or (anhydrous) sulfuric acid is present in an amount of 1.4 to 10 moles per one mole of elemental rhodium, to obtain 4-tert.-butylcyclohexanol, and then acetylating 4-tert.-butylcyclohexanol to obtain 4-tert.-butylcyclohexyl acetate.

DETAILED DESCRIPTION OF THE INVENTION

The rhodium catalyst to be used in the hydrogenation in the present invention is at least one rhodium catalyst selected from the group consisting of metal rhodium (valency of zero) and rhodium compounds (having a valency of up to 6 such as rhodium chloride, rhodium oxide and son on) supported on a carrier such as activated carbon, $SiO_2$, $Al_2O_3$, etc. Among them, metal rhodium supported on the carrier is preferred. In the case of the use of metal rhodium, the supported amount of metal rhodium usually falls within the range of from 1 to 10 wt. %, preferably falls within the range of from 3 to 5 wt. %, based on the weight of the carrier.

The amount of the rhodium catalyst to be used in the reaction usually falls within the range of from about 0.01 to 1 wt. % (in terms of elemental rhodium) based on the weight of 4-tert.-butylphenol. The amount of the catalyst (including the carrier) depends on the supported amount of the metal rhodium or rhodium compounds, and it usually falls within the range of from about 0.1 to 50 wt. % (in terms of the dry rhodium catalyst) based on the weight of 4-tert.-butylphenol. When the amount of the catalyst to be used is large, the selectivity of the cis-isomer of 4-tert.-butylcyclohexanol is high.

The amount of the catalyst preferably falls within the range of from 0.5 to 10 wt. % in view of the cost and workability in the filtration step for recovering the catalyst.

After the reaction, the rhodium catalyst may be recovered from a reaction mixture by a conventional method such as filtration, decantation, centrifugation, and may be reused.

Any solvent may be used for the hydrogenation as long as it has no adverse effect on the hydrogenation. Solvents which are in the liquid state at room temperature (25° C.) are preferred because of easy handling. Examples of the solvents are alkanes having 5 to 10 carbon atoms, ethers having 4 to 10 carbon atoms, alcohols having 1 to 6 carbon atoms, and so on. Specific examples of the solvents are acyclic alkanes (e.g. pentane, hexane, heptane, etc.), cyclic alkanes (e.g. cyclohexane, etc.), acyclic ethers (e.g. diethyl ether, etc.), cyclic ethers (e.g. tetrahydrofuran, dioxane, etc.), and alcohols (e.g. methanol, ethanol propanol, isopropanol, butanol, isobutanol, pentanol, hexanol, 4-methyl-2-pentanol, cyclohexanol, etc.). Among them, cyclohexane and isopropanol are preferred. In particular, isopropanol is preferred.

The amount of the solvent to be used for the hydrogenation usually falls within the range of from about 0.2 to 20 times, preferably within the range of from 0.4 to 5 times the weight of 4-tert.-butylphenol.

In the process of the hydrogenation of the present invention, the reaction is performed in a solvent in the presence of a rhodium catalyst and also a compound selected from the group consisting of hydrogen chloride and (anhydrous) sulfuric acid.

Hydrogen chloride may be supplied in the reaction system in any form, for example, by bubbling hydrogen chloride gas through the reaction system, or adding hydrochloric acid to the reaction system. Alternatively, hydrochloric acid may be formed in the reaction system, for example, by charging water and $AlCl_3$ or $TiCl_4$ to the reaction system.

Also, (anhydrous) sulfuric acid may be supplied in the reaction system in any form, for example, by bubbling $SO_3$ gas through the reaction system or adding an aqueous sulfuric acid solution to the reaction system.

The order of the addition of 4-tert.-butylphenol, the rhodium catalyst, the solvent and hydrogen chloride or (anhydrous) sulfuric acid is arbitrary.

The amount of hydrogen chloride or (anhydrous) sulfuric acid usually falls within the range of from 0.01 to 100 moles, preferably from 0.05 to 10 moles, more preferably from 0.1 to 10 moles, per one mole of elemental rhodium in the rhodium catalyst.

The hydrogenation of the present invention may be carried out in a stream of hydrogen gas or in a pressurized hydrogen atmosphere. Other reaction conditions may not be critical. In view of a reaction rate, the reaction is preferably carried out in the pressurized hydrogen atmosphere. In this case, a pressure reactor is used.

When the hydrogen atmosphere is carried out under the pressurized hydrogen atmosphere, the partial pressure of hydrogen is usually at least about $1.5 \times 10^3$ Pa. In view of the reaction rate, the selectivity of the cis-isomer and the pressure resistance of the equipment, the partial pressure of hydrogen preferably falls within the range of from $3 \times 10^3$ to $2 \times 10^6$ Pa, more preferably from $5 \times 10^5$ to $1.5 \times 10^6$ Pa.

The reaction temperature of the hydrogenation is preferably about 20° C. or more in view of the reaction rate and the selectivity of the cis-isomer, and about 100° C. or lower in view of the selectivity of the cis-isomer. More preferably, the reaction temperature falls within the range of from 40° C. to 80° C. in view of both the reaction rate and the selectivity of the cis-isomer.

The termination of the hydrogenation can be confirmed by a conventional method. For example, the reaction mixture is analyzed and a time when the conversion of 4-tert.-butylphenol is about 100% is used as the termination of the hydrogenation, or a time when no further decrease of the hydrogen pressure is observed is used as the termination of the hydrogenation.

Furthermore, 4-tert.-butylcyclohexanol obtained by the above hydrogenation can be acetylated to obtain 4-tert.-butylcyclohexyl acetate.

The acetylation can be performed continuously from the above hydrogenation of 4-tert.-butylphenol. Alternatively, 4-tert.-butylcyclohexanol obtained by the above hydrogenation can be once isolated from the reaction mixture and then acetylated in a separate step.

For the acetylation, any conventional acetylation agent such as acetic anhydride, acetic acid, acetyl chloride, and the like may be used.

The amount of the acetylation agent to be used usually falls within the range of from 1 mole to 5 moles, preferably falls within the range of from 1 mole to 1.5 moles, per one mole of 4-tert.-butylcyclohexanol.

The reaction temperature of the acetylation usually falls within the range of from room temperature (about 25° C.) to 150° C., preferably falls within the range of from room temperature (about 25° C.) to 130° C.

The termination of the acetylation can be confirmed by a conventional method. For example, a time when the conversion of 4-tert.-butylcyclohexanol is about 100% is used as the termination of acetylation through the analysis of the reaction mixture.

The presence of a solvent is not essential in the acetylation process, and a solvent which is less acetylated may be used. Solvents which are in the liquid state at room temperature are preferred in view of easy handling. Examples of such solvents are alkanes having 5 to 10 carbon atoms, ethers having 4 to 10 carbon atoms, and so on. Specific examples of the solvents are acyclic alkanes (e.g. pentane, hexane, heptane, etc.), cyclic alkanes (e.g. cyclohexane, etc.), unsaturated hydrocarbons (e.g. toluene, etc.), acyclic ethers (e.g. diethyl ether, etc.), cyclic ethers (e.g. tetrahydrofuran, etc.), and the like. Among them, toluene and cyclohexane are preferred.

The acetylation of the present invention may be carried out in the presence of a catalyst. The kind of the catalyst depends on the acetylation agent to be used. For example, sulfuric acid, hydrochloric acid, p-toluenesulfonic acid, zinc chloride, sodium acetate, pyridine, and the like can be used, when acetic anhydride is used as the acetylation agent. Sulfuric acid and the like can be used, when acetic acid is used as the acetylation agent. Among these catalysts, sulfuric acid is preferred in view of a cost.

The amount of the catalyst usually falls within the range of from 0.01 to 5 mole %, preferably from 0.1 to 2 mole %, of the amount of 4-tert.-butylcyclohexanol. When the amount of the catalyst to be used is too large, 4-tert.-butylcyclohexanol tends to be dehydrated.

When acetic acid is used as the acetylation agent, the acetylation is preferably carried out while removing by-produces water in view of the reaction rate. Water may be removed, for example, by evaporating water azeotropically with a solvent which can form an azeotrope with water under refluxing conditions, or by adding a drying agent such as silica gel to the reaction system.

When acetyl chloride is used as the acetylation agent, the acetylation is preferably carried out while removing by-produced hydrogen chloride in view of safety. Hydrogen chloride may be removed, for example, by adding a base such as inorganic bases (e.g. potassium carbonate, sodium hydroxide, etc.) and organic bases (e.g. pyridine, etc.) to the reaction system.

Among the acetylating agents, acetic anhydride is preferably used for the acetylation in view of the conversion of 4-tert.-butylcyclohexanol.

It is difficult to separate resulting 4-tert.-butylcyclohexyl acetate from 4-tert.-butylcyclohexanol by distillation since they have the close boiling points. Therefore, the conversion of 4-tert.-butylcyclohexanol is preferably equal or close to 100%. To this end, for example, acetic acid or acetyl chloride is used as the acetylation agent and the acetylation is carried out until the conversion of 4-tert.-butylcyclohexanol reaches about 90% or higher, and then the acetylation is completed with acetic anhydride in the same molar amount as the residual 4-tert.-butylcyclohexanol so that 4-tert.-butylcyclohexanol is consumed completely.

After the acetylation, 4-tert.-butylcyclohexyl acetate may be recovered from the reaction mixture by a conventional method such as rectification. Before the rectification, the reaction mixture may be washed with, for example, aqueous sodium bicarbonate and water.

The processes of hydrogenation and acetylation of the present invention may be carried out continuously or batch-wise.

According to the processes of the present invention, 4-tert.-butylcyclohexanol having the high content of the cix-isomer which is useful as a raw material for a perfume can be easily obtained from 4-tert.-butylphenol. That is, 4-tert.-butylcyclohexanol can be usually obtained in a yield of about 90% or higher, and the content of the cis-isomer thereof usually reaches about 80% or more. 4-tert.-Butylcyclohexyl acetate having the high content of the cis-isomer thereof can be obtained by acetylating 4-tert.-butylcyclohexanol which has been prepared by the process of the present invention.

EXAMPLES

The present invention will be described in detail below with reference to Examples, but the present invention is not no way limited thereto.

Example 1

4-tert.-Butylphenol (90 g, 0.60 mole), 5% Rh/C (5 wt. % of metal rhodium supported on an activated carbon carrier; standard grade produced by N. E. CHEMCAT Co. Ltd.) (1.35 g in terms of the dry rhodium catalyst), isopropanol (180 g) and 36% hydrochloric acid (0.18 g) were charged into an autoclave, and then the interior of the autoclave was replaced with nitrogen gas by injecting the nitrogen gas up to $5 \times 10^5$ Pa and evacuating it three times. After replacing the interior of the autoclave with hydrogen by injecting the hydrogen gas up to $5 \times 10^6$ Pa and evacuating it three times, the hydrogen gas was injected up to $1.1 \times 10^6$ Pa, and an interior temperature was raised to 60° C., followed by stirring for 1.75 hours.

After cooling the autoclave and replacing the interior with the nitrogen gas in the same way as above, the reaction mixture was analyzed. The yield of 4-tert.-butylcyclohexanol was 93.4%, and the ratio of the cis-isomer to trans-isomer was 89.9:10.1.

Examples 2–10

4-tert.-Butylcyclohexanol was prepared in the same manner as in Example 1 except that the reaction conditions were changed as shown in Table 1. In Example 10, 98% sulfuric acid was used. The results are shown in Table 1.

In Examples 1–10, the conversion of 4-tert.-butylphenol was 100%.

Comparative Examples 1–3

4-tert.-Butylcyclohexanol was prepared in the same manner as in Example 1 except that the reaction conditions were changed as shown in Table 2, and no acid was used (Comparative Example 1), 85% phosphoric acid was used (Comparative Example 2), or 61% nitric acid was used (Comparative Example 3), respectively. The results are shown in Table 2.

Comparative Examples 4 and 5

4-tert.-Butylcyclohexanol was prepared in the same manner as in Example 1 except that the reaction conditions were changed as shown in Table 2, and a Ru catalyst (5% Ru/C) was used (Comparative Examples 4 and 5) and no hydrochloric acid was used (Comparative Example 5), respectively. The results are shown in the Table 2. In Comparative Example 4, the conversion of 4-tert.-butylphenol was 42.2%, while in other Comparative Examples, the conversion of 4-tert.-butylphenol was 100%.

TABLE 1

| | Catalyst | | Acid | Amount (molar ratio to Rh) | Solvent | | Hydrogen partial pressure × $10^5$ Pa | Temp. (°C.) | Time (hr) | BCHL[3] | |
|---|---|---|---|---|---|---|---|---|---|---|---|
| Ex. No. | Kind | Amount (g) | Kind | (g) | | Kind | Amount (g) | | | | Yield (%) | cis/trans ratio |
| 1 | Rh | 1.35 | 36% HCl | 0.18 | 2.7 | IPA[1] | 180 | 11 | 60 | 1.75 | 93.4 | 89.9/10.1 |
| 2 | Rh | 0.90 | 36% HCl | 0.12 | 2.7 | IPA | 180 | 11 | 60 | 3.0 | 93.4 | 87.8/12.2 |
| 3 | Rh | 2.25 | 36% HCl | 0.30 | 2.7 | IPA | 74 | 23 | 40 | 5.0 | 93.0 | 86.3/13.7 |
| 4 | Rh | 1.45 | 36% HCl | 0.18 | 2.5 | CHX[2] | 180 | 13 | 60 | 1.2 | 96.3 | 86.3/13.7 |
| 5 | Rh | 2.25 | 36% HCl | 0.30 | 2.7 | CHX | 360 | 6 | 40 | 0.6 | 96.0 | 87.6/12.4 |
| 6 | Rh | 2.25 | 36% HCl | 0.30 | 2.7 | CHX | 74 | 41 | 40 | 0.3 | 96.1 | 86.6/13.4 |
| 7 | Rh | 2.25 | 36% HCl | 0.30 | 2.7 | CHX | 74 | 21 | 80 | 0.5 | 96.6 | 84.1/15.9 |
| 8 | Rh | 2.25 | 36% HCl | 0.60 | 5.4 | CHX | 74 | 21 | 40 | 1.0 | 94.6 | 89.8/10.2 |
| 9 | Rh | 4.50 | 36% HCl | 0.60 | 2.7 | CHX | 74 | 21 | 40 | 0.5 | 95.9 | 91.2/8.8 |
| 10 | Rh | 2.19 | 98% $H_2SO_4$ | 0.15 | 1.4 | CHX | 74 | 21 | 40 | 0.5 | 97.0 | 79.9/20.1 |

Notes:
[1]IPA: Isopropanol
[2]CHX: Cyclohexane
[3]BCHL: 4-tert.-Butylcyclohexanol

TABLE 2

| Co. Ex. No. | Catalyst Kind | Amount (g) | Acid Kind | Amount (g) | Solvent Kind | Amount (g) | Hydrogen partial pressure × $10^5$ Pa | Temp. (°C.) | Time (hr) | Yield (%) | BCHL[2] cis/trans ratio |
|---|---|---|---|---|---|---|---|---|---|---|---|
| 1 | Rh | 4.50 | None | 0 | CHX[1] | 74 | 21 | 40 | 0.3 | 96.6 | 68.5/31.5 |
| 2 | Rh | 2.25 | 85% $H_3PO_4$ | 0.23 | CHX | 74 | 21 | 40 | 0.7 | 97.0 | 68.6/31.4 |
| 3 | Rh | 2.19 | 61% $HNO_3$ | 0.31 | CHX | 74 | 21 | 40 | 7.0 | 69.9 | 60.7/39.3 |
| 4 | Rh | 4.50 | 36% HCl | 0.30 | CHX | 74 | 21 | 40 | 10.0 | 39.8 | 68.3/31.7 |
| 5 | Rh | 4.50 | None | 0 | CHX | 74 | 21 | 40 | 1.5 | 97.8 | 63.2/36.8 |

Notes:
[1] CHX: Cyclohexane
[2] BCHL: 4-tert.-Butylcyclohexanol

Example 11

4-tert.-Butylphenol (90 g, 0.60 moles), 5% Rh/C (standard grade produced by N. E. CHEMCAT Co. Ltd.) (2.25 g in terms of the dry rhodium catalyst), cyclohexane (74 g) and 36% hydrochloric acid (0.30 g) were charged into an autoclave. The interior of the autoclave was replaced with nitrogen gas by injecting the nitrogen gas up to $5 \times 10^5$ Pa and evacuating it three times. After replacing the interior of the autoclave with hydrogen by injecting the hydrogen gas up to $5 \times 10^6$ Pa and evacuating it three times, the hydrogen gas was injected up to $2.1 \times 10^6$ Pa, and an interior temperature was raised to 40° C., followed by stirring for 0.75 hours.

After cooling the autoclave and replacing the interior with the nitrogen gas in the same way as above, the reaction mixture was analyzed. The yield of 4-tert.-butylcyclohexanol was 95.8%, and the ratio of the cis-isomer to trans-isomer was 88.3:11.7.

The reaction mixture was filtrated to remove the rhodium catalyst, and was concentrated. Sulfuric acid (0.17 g, 1.7 mmole) was added to the above concentrated mixture while maintaining a temperature of the mixture at 90° C., and then acetic anhydride (64.3 g, 0.60 mole) was dropwise added to the mixture over 3 hours, followed by keeping that temperature for 1 hour.

The analysis of the reaction mixture revealed that the yield of 4-tert.-butylcyclohexyl acetate was 97.1% (based on 4-tert.-butylcyclohexanol), and the ratio of the cis-isomer to trans-isomer was 87.2:12.8.

What is claimed is:

1. A process for preparing 4-tert.-butylcyclohexanol comprising hydrogenating 4-tert.-butylphenol in a solvent in the presence of (1) at least one rhodium catalyst selected from the group consisting of metal rhodium and rhodium compounds supported on a carrier, and (2) a compound selected from the group consisting of hydrogen chloride and (anhydrous) sulfuric acid, wherein hydrogen chloride or (anhydrous) sulfuric acid is present in an amount of 1.4 to 10 moles per one mole of elemental rhodium.

2. The process according to claim 1, wherein said rhodium catalyst comprises metal rhodium supported on a carrier.

3. The process according to claim 2, wherein an amount of the rhodium catalyst (in terms of the dry rhodium catalyst) is from 0.5 to 10 wt. % based on the weight of 4-tert.-butylphenol.

4. The process according to claim 1, wherein said solvent is a solvent selected from the group consisting of alkanes having 5 to 10 carbon atoms, ethers having 4 to 10 carbon atoms and alcohols having 1 to 6 carbon atoms.

5. The process according to claim 4, wherein said solvent is an alcohol.

6. The process according to claim 5, wherein said alcohol is isopropanol.

7. The process according to claim 1, wherein a reaction temperature is from 20 to 100° C.

8. The process according to claim 1, wherein said carrier is activated carbon.

9. A process for preparing 4-tert.-butylcyclohexyl acetate comprising the steps of:

hydrogenating 4-tert.-butylphenol in a solvent in the presence of (1) at least one rhodium catalyst selected from the group consisting of metal rhodium and rhodium compounds supported on a carrier and (2) a compound selected from the group consisting of hydrogen chloride and (anhydrous) sulfuric acid, wherein hydrogen chloride or (anhydrous) sulfuric acid is present in an amount of 1.4 to 10 moles per one mole of elemental rhodium, to obtain 4-tert.-butylcyclohexanol, and then acetylating 4-tert.-butylcyclohexanol to obtain 4-tert.-butylcyclohexyl acetate.

* * * * *